United States Patent
Orfao de Matos Correia e Vale

(10) Patent No.: US 6,913,901 B2
(45) Date of Patent: Jul. 5, 2005

(54) PROCEDURE FOR CONTROLLING THE ENUMERATION OF THE ABSOLUTE COUNT OF CELLS OR OTHER PARTICLES PRESENT IN A SAMPLE

(75) Inventor: José Alberto Orfao de Matos Correia e Vale, Salamanca (ES)

(73) Assignee: Universidad de Salamanca (ES)

( * ) Notice: Subject to any disclaimer, the term of this patent is extended or adjusted under 35 U.S.C. 154(b) by 331 days.

(21) Appl. No.: 10/078,558

(22) Filed: Feb. 14, 2002

(65) Prior Publication Data

US 2002/0115130 A1 Aug. 22, 2002

(30) Foreign Application Priority Data

Feb. 20, 2001 (ES) .......................................... 200100376

(51) Int. Cl.[7] ............................ C12Q 1/02; C12P 35/06
(52) U.S. Cl. ........................................... 435/29; 435/49
(58) Field of Search ............................... 435/29, 49, 39

(56) References Cited

U.S. PATENT DOCUMENTS 5,882,863 A * 3/1999 Imai et al. ...................... 435/6

FOREIGN PATENT DOCUMENTS

| EP | 0586183 | 3/1994 | .................... 33/58 |
|----|---------|--------|--------------------------|
| EP | 0586183 A1 * | 9/1994 | |
| FR | 2795820 | 1/2001 | .................... 15/10 |

OTHER PUBLICATIONS

European Search Report EP 02 38 0032 dated Apr. 23, 2002.
"Cytofluorometric Methods for Assessing Absolute Numbers of Cell Subsets In Blood", Bruno Brando et al., pp. 327–345.

* cited by examiner

Primary Examiner—Bruce R. Campell
Assistant Examiner—Randall Winston
(74) Attorney, Agent, or Firm—Ostrolenk, Faber, Gerb & Soffen, LLP

(57) ABSTRACT

Procedure for controlling the enumeration of the absolute count of cells (or other particles) present in a sample. The procedure consists of the following: to prepare, in known quantities and proportions, a mixture or stock solution of two or more populations of reference particles of differing characteristics; to add a known quantity of this mixture of reference particles to a known volume of the sample which contains the cells (or other particles) to be counted; to measure, in a flow cytometer, the sample containing both the cells (or other particles), the events of which are to be counted, and the mixture of different populations of reference particles; to calculate the absolute number of cells (or other particles) present in the sample to be counted and; to check that the proportion between the different reference particles present in the sample measured concurs with the proportion that exists between them in the initial mixture or stock solution which contained the different populations of reference particles prior to adding it to the sample.

20 Claims, No Drawings

PROCEDURE FOR CONTROLLING THE ENUMERATION OF THE ABSOLUTE COUNT OF CELLS OR OTHER PARTICLES PRESENT IN A SAMPLE

BACKGROUND OF THE INVENTION

The invention mainly, but not exclusively, relates to a simple, rapid and precise procedure for controlling the absolute number of cells (or other particles) in suspension found per unit volume of a sample.

The procedure of the invention makes use of a flow cytometer equipped with one or more lasers and is based on the use of a mixture of different populations of reference particles, in known quantities and proportions. The procedure is of use for research, diagnostic, prognostic purposes and to evaluate therapeutic protocols.

Enumeration of absolute counts of cells (or other particles) of a sample, represents information of utmost importance both in biomedical research and in clinical diagnostic laboratories.

Currently, a number of different methods are available for the enumeration of absolute cell counts present in a sample, the most accurate and precise of which use samples where the particles to be counted are in suspension. Of these, the most notable techniques employ two types of instruments: hematological analyzers and flow cytometers.

While the hematological analyzers employ volumetric methods for the counting of particles detected through the measurement of the impedance and more recently through the light scatter of a laser, the principles behind the enumeration of absolute counts of cells or other particles in flow cytometers are diverse and include various volumetric methods or the use of reference particles.

Though the flow cytometry volumetric methods for the enumeration of absolute counts of cells or other particles can only be applied in a limited number of instruments, with only two commercially available at present, methods based on the the use of reference particles can be applied to any flow cytometer independently of the manufacturer, including the most popular models.

Through this latter method, we can determine the number of cells (or other particles) present in a defined volume of a sample, adding a defined number of reference particles to a certain volume, also pre-determined, of the sample. The accuracy of the method depends on the preparation of the mixture of reference particles and the measurement of the volume of the sample, independently of the possible addition to the former mixture of variable volumes of other reagents that make measurements more difficult, such as monoclonal antibodies to identify the cells of interest or lysing solutions which specifically destroy non-nucleated cells (for example, the red blood cells in samples used to study leukocytes).

Without doubt, the most critical steps in this technique are 1) the precise measurement of a determined volume of the sample.
2) the mixture with the sample of a precise number of reference particles.

Currently, there are two ways to approach the latter question:
i) add a known volume of the sample to tubes containing lyophilized reference microbeads—TRUCOUNT™ tubes—or, alternatively ii) to add to a tube containing a known volume of the sample, an accurately measured volume of a solution which contains, in suspension, a known number of particles or microbeads—FLOWCOUNT™ spheres. In the latter, it is assumed that the stock solution of FLOWCOUNT™ microbeads from which a precise volume is pipetted and which has been previously vortexed, contains a homogeneously distributed suspension of reference microbeads. At the same time, in both methods—FLOWCOUNT™ and TRUCOUNT™—it is assumed that during measurement no preferential selection exists either of the reference microbeads or of the cells (or other particles) present in the sample from which the count is to be made.

In recent years, both methods for calculating the absolute count of particles have been adopted for use, initially by research laboratories but, subsequently, by clinical diagnostic laboratories too. Among other uses, they have been employed for the count of $CD4^+$ T-lymphocytes in peripheral blood of individuals infected with human immunodeficiency virus (HIV), as well as of $CD34^+$ stem and hematopoietic precursor cells in leukapheresis products in order to predict the success or failure of a prospective transplant. Preliminary studies have shown that disturbing levels of variability exist in these types of measurements which are usually reduced with the training of the personnel responsible for carrying out the technique.

Despite partial standardization of the techniques and methods described above, until now, in these types of measurements there has been no procedure described which would address the control of two significant variables:

1) the homogenous distribution of the reference particles, both in the stock solution and once mixed with the sample to be measured.
2) the selective acquisition of cells or reference particles during measurement in the flow cytometer.

SUMMARY AND DESCRIPTION OF THE INVENTION

Therefore, an objective of this invention consists in proposing a solution which will successfully control for these two variables, which may affect the enumeration of the absolute counts of cells/particles in suspension in a sample, without requiring additional measurements.

Equally, another objective of the invention consists in controlling for the possible existence of specific-negative or-positive selection of the cells (or other particles) in the sample to be counted, during the measurement process itself.

Consequently, the present invention represents a procedure for the control of the flow cytometry process of enumerating absolute counts of cells (or other particles) per unit volume of sample, based on the use of a mixture of two or more types of reference particles of differing characteristics. This procedure is characterized by the following stages:

a) to prepare a mixture or stock solution in known quantities and proportions, of two or more populations of reference particles of distinct characteristics;
b) to add a known quantity of this mixture of reference particles to a known volume of the sample containing the cells (or other particles) to be counted;
c) to measure in a flow cytometer, the sample containing the reference particles.
d) to calculate the absolute number of cells (or other particles) present in the sample to be counted;
e) to check that the proportion between the different populations of reference particles in the sample measured, concurs with that which exists in the initial mixture or stock solution containing the different populations of reference particles.

For the purpose of this invention, by the expression "reference particles of distinct characteristics", it is understood that the particles have different characteristics, for example, in terms of their differing densities and/or adhesive properties and/or light scatter and/or fluorescence properties.

For the purposes of this invention, the preparation of the sample for specific identification of cells (or other particles) of interest, previous to their count, the selection of the cells (or other particles) of interest, as well as the calibration and adjustment of the flow cytometer, are carried out according to methods widely described and recommended for the characterization of cells or other particles using a flow cytometer.

For the analysis of the results and for the accurate quantification of each subpopulation of cells (or other particles) of interest and each of the populations of reference particles, various computer programs may be used, such as Cell Quest™, Paint-A Gate, PRO™ or Expo 32™.

The procedure for this invention can be used both in normal and pathological samples, for all purposes that require the controlled count of cells (or other particles) present in a sample, including counts for research, diagnostic and prognostic purposes and for therapeutic evaluation.

As indicated by the procedure described above, the number of populations of reference particles may vary, as can the proportion and absolute quantity of each population and their physical and chemical characteristics. In the same way, it is understood that the invention covers variations in the order in which the mixture of the sample with reference populations of particles is carried out (putting the reference particles in a receptacle containing the sample for analysis or vice-versa), and that different stock solutions may contain each population of reference particles of a known quantity and concentration, or that the stock solution may contain the reference particles already mixed.

From the above it may be assumed that the chemical compound, the form, size, volume, density, adhesion capacity, fluorescence, transparence, refractory index or other characteristics of each population of reference particles used, may vary depending on the type of cells (or other particles) of the sample to be counted. In the same way, it is understood that each population of reference particles may contain varied quantities of one or more fluorescent compounds or compounds that absorb light inside or on their surface.

With this invention, as the cells (or other particles) of interest within the sample are being counted, at the same time, there is a successful control of any heterogeneous distribution of populations of reference particles when mixed with the sample, and of any selective acquisition of cells (or other particles) during measurement within the flow cytometer.

Below, the invention will be illustrated through an example which in no way limits the area of its application:
Material and Methods: Obtaining the Sample Peripheral blood was collected from 10 healthy donors mobilized with G-CSF over five days, in VACUTAINER™ tubes containing tri-potassic (K3) EDTA as an anticoagulant. The tubes were maintained at room temperature until the beginning of sample preparation for the enumeration of CD34$^+$ stem and hematopoietic progenitor cells (HPC).

The enumeration of the absolute count of CD34$^+$ HPC was carried out in all cases within a period of two hours after obtaining the samples.

Producing a Mixture of Particles or Reference Microbeads (Stock solution of Reference Particles)

In order to make up the mixture of microbeads, two separate solutions, each containing a different type of microbead at a different concentration were used. The first solution contained polystyrene microbeads of a diameter of 6.4±0.1 µm, and a density of 1.06±0.02 marked with fluorescein isothiocyanate (FITC) at a concentration known to be 1500 microbeads/µL of solution. The second solution contained polystyrene microbeads with 10% metacrylate of a diameter of 6.2±0.1 µm, with a density of 1.050±0.03, which have been conjugated with phycoerythrin at a concentration known to be 500 microbeads/µL of solution. Using a reverse pipetting technique, a mixture (stock solution of reference particles) was prepared of equal parts (1/1 v/v) of the two aforementioned solutions containing a final concentration of 1,000 microbeads/µL; of these, 750 microbeads/µL corresponded to polystyrene microbeads, and 250 microspheres/µL to polystyrene/metacrylate microbeads. Both groups of spheres displayed different fluorescent characteristics which permitted the individual identification of each type of microbead in a bi-dimensional representation of green fluorescence ($FL_1$) versus orange fluorescence ($FL_2$).

Preparation of Samples

For each sample two tubes were prepared in parallel. In each of them, 100 µl of peripheral blood was added, using a reverse pipetting technique employing a digital pipette, calibrated prior to sample preparation in order to accurately measure the volumes of 100 µl. Then, to each tube, 20µl of anti-CD45 monoclonal antibody, conjugated with allophycocyanin (APC) (HLE-1 clone, Becton Dickinson Biosciences, San Jose, Calif., USA) was added. Furthermore, to one tube 20 µl of a mouse monoclonal antibody ($IgG_1$) anti-CD34 conjugated with phycoerythrin (HPCA-2 clone, Becton Dickinson Biosciences) was added, while to the second tube, instead of this antibody, 20 µl of an IgG1 mouse immunoglobulin conjugated with phycoerythrin without specific reactivity for the antigens present in human cells, was added; this latter tube was used as a negative isotypic control.

After gently vortexing for five seconds, both tubes were incubated for 15 minutes at room temperature in the dark. After incubation, to each tube 2 ml of the fixative-free QUICKLYSIS (Cytognos, Salamanca, Spain) hypotonic solution was added and a second period of incubation was carried out at room temperature in the dark for 10 minutes. Immediately after this incubation, 100 µl of the mixed solution of reference microbeads (stock solution) was added to each tube, after gentle mixing in a horizontal homogenizer. Then, both tubes were placed in a horizontal homogenizer and gently mixed for 1 minute in order to achieve a homogenous distribution both of the CD34$^+$ cells to be counted and the two subpopulations of reference microbeads added to the stained sample.

Data Acquisition and Analysis

Once the mixture of the sample with reference particles had been homogenized, the light scatter and fluorescence characteristics of both the cells and reference particles present in the two tubes, prepared for each sample in accordance with the aforementioned method, were measured. In order to achieve this, a FACSCalibur flow cytometer (Becton Dickinson Biosciences) equipped with an argon laser and a photodiode with light emissions tuned at 488 nm and 630 nm, respectively, was used. Prior to measurement, the flow cytometer was calibrated following the manufacturer's instructions and specifications using CALIBRITE BEADS™ (Becton Dickinson Biosciences). For data acquisition, the threshold was set at FSC (forward light scatter) at channel 50 (arbitrary units scaled from 0 to 1023 channels). For each tube, information was gathered on 100,000 events, using the CellQUEST™ software program (Becton Dickinson Biosciences).

Identification of CD34$^+$ hematopoietic precursor cells was carried out based on the intense expression of CD34-PE (FL2$^{++}$), weak reactivity for CD45-APC (FL4$^+$-) and intermediate values of FSC and SSC (side light scatter). In turn, the two subpopulations of microbeads were identified by their low FSC values with high SSC together with both green (FL1$^{+/+++}$) and orange (FL$^{+/++}$) fluorescence.

The specific identification within the reference particles of each of the two different populations of reference microbeads, was carried out based on their different fluorescence characteristics: population 1 was FL1$^{+++}$/FL2$^+$ and population 2 was FL1$^+$/FL2$^{++}$.

Once the events corresponding to CD34$^+$ HPC on the one hand, and the two populations of reference particles on the other hand, had been identified, it was checked that population 1 of reference particles consisted of a number of events three times greater than that of population 2.

The absolute number of CD34$^+$ cells/µl of sample was calculated using the following formula:

$$N. \text{ of CD34}^+ \text{ cells}/\mu l = 1,000 \text{ (N. of microbeads added to each tube/} \mu l \text{ of sample)} \times N.$$

of events corresponding to CD34$^+$ cells/N. of events which correspond to the total of the two populations of microbeads.

What is claimed is:

1. A method to control a count of particles per unit volume to be counted in a sample, the method comprising the steps of:
   preparing a first mixture of a plurality of populations of reference particles in known proportions and known quantities, the reference particles in each of the populations having at least one respective characteristic differing between the populations;
   adding a known quantity of the first mixture to a known volume of the sample to produce a second mixture containing the particles to be counted and the populations of reference particles;
   flowing the second mixture past a measuring device:
   measuring with the measuring device a count of the particles to be counted and a count of the reference particles of each of the populations of reference particles in the second mixture in the flow past the measuring device;
   calculating an absolute number of the particles to be counted per unit volume in the second mixture from the counts of the particles to be counted in the sample and the reference particles;
   determining final proportions of the populations of the reference particles in the second mixture; and
   checking whether the final proportions between the populations of the reference particles in the second mixture correspond to the known proportions between the populations of the reference particles in the first mixture to determine the accuracy of the calculated number of the particles to be counted per unit volume in the second mixture.

2. The method of claim 1, wherein the particles to be counted are cells.

3. The method of claim 1, wherein the at least one characteristic differing between the reference particles is a light scatter characteristic.

4. The method of claim 1, wherein the at least one characteristic differing between the reference particles is a chemical composition characteristic.

5. The method of claim 1, wherein the at least one characteristic differing between the reference particles is a form characteristic.

6. The method of claim 1, wherein the at least one characteristic differing between the reference particles is a size characteristic.

7. The method of claim 1, wherein the at least one characteristic differing between the reference particles is a volume characteristic.

8. The method of claim 1, wherein the at least one characteristic differing between the reference particles is a density characteristic.

9. The method of claim 1, wherein the at least one characteristic differing between the reference particles is an adhesive characteristic.

10. The method of claim 1, wherein the at least one characteristic differing between the reference particles is a fluorescence characteristic.

11. The method of claim 1, wherein the at least one characteristic differing between the reference particles is a characteristic to permit a detection of a selective acquisition of the particles to be counted during the measuring step.

12. The method of claim 1, wherein the sample includes at least one of a normal sample and a pathological sample, the sample one of obtained ex-vivo, stored, and treated in-vitro.

13. The method of claim 1, wherein the adding step includes the following sub-steps:
    adding the sample to a receptacle; and
    adding the known quantity of the first mixture to the receptacle after adding the sample to the receptacle.

14. The method of claim 1, wherein the adding step includes the following sub-steps:
    adding the known quantity of the first mixture to a receptacle; and
    adding the sample to the receptacle after adding the known quantity of the first mixture to the receptacle.

15. The method of claim 1, wherein the at least one characteristic differing between the populations the reference particles is selected in accordance with a type of the particles to be counted.

16. The method of claim 15, wherein the at least one characteristic differing between the populations of the reference particles is selected from the group consisting of at least one of a chemical composition characteristic, a form characteristic, a volume characteristic, a size characteristic, a density characteristic, an adhesion characteristic, a fluorescence characteristic, a transparence characteristic, and a refractory index characteristic.

17. The method of claim 1, wherein the populations of reference particles include variable quantities of at least one compound, the compound including at least one of a flourescent compound and a compound that absorbs light.

18. The method of claim 1, wherein the first mixture includes a stock mixture.

19. The method of claim 1,
    wherein the checking step determines at least one of
        whether the adding step produced a heterogeneous distribution of the reference particles, and
        whether a selective acquisition of the reference particles occurred during the measuring step.

20. The method of claim 1, wherein the measuring device is a flow cytometer and the flowing comprises flowing the second mixture past the flow cytometer.

* * * * *